United States Patent
Degen et al.

(10) Patent No.: US 9,577,459 B2
(45) Date of Patent: Feb. 21, 2017

(54) SYSTEMS AND METHODS FOR REGULATING INDUCTIVE ENERGY TRANSFER TO AN IMPLANTABLE SYSTEM

(71) Applicant: SEQUANA MEDICAL AG, Zug OT (CH)

(72) Inventors: Thomas Werner Degen, Birmensdorf (CH); Stefan Tschumper, Jona (CH)

(73) Assignee: Sequana Medical AG, Zug (CH)

( * ) Notice: Subject to any disclaimer, the term of this patent is extended or adjusted under 35 U.S.C. 154(b) by 484 days.

(21) Appl. No.: 13/831,642

(22) Filed: Mar. 15, 2013

(65) Prior Publication Data

US 2014/0266022 A1  Sep. 18, 2014

(51) Int. Cl.
| | |
|---|---|
| H02J 7/00 | (2006.01) |
| H02J 7/02 | (2016.01) |
| A61M 5/142 | (2006.01) |
| A61N 1/378 | (2006.01) |
| A61M 27/00 | (2006.01) |

(52) U.S. Cl.
CPC .......... *H02J 7/025* (2013.01); *A61M 5/14276* (2013.01); *A61N 1/3787* (2013.01); *H02J 7/007* (2013.01); *A61M 2027/004* (2013.01); *A61M 2205/3538* (2013.01); *A61M 2205/3569* (2013.01); *A61M 2205/8243* (2013.01)

(58) Field of Classification Search
CPC .............. A61M 2205/8243; A61M 2205/8237
USPC ....................................................... 361/91.6
See application file for complete search history.

(56) References Cited

U.S. PATENT DOCUMENTS

| | | | | |
|---|---|---|---|---|
| 4,347,543 A | * | 8/1982 | Frister et al. | 361/91.6 |
| 4,594,631 A | * | 6/1986 | Iwaki | 361/20 |
| 7,311,690 B2 | | 12/2007 | Burnett | |
| 7,909,790 B2 | | 3/2011 | Burnett | |
| 8,202,248 B2 | | 6/2012 | Burnett et al. | |
| 8,394,048 B2 | | 3/2013 | Burnett | |
| 8,398,577 B2 | | 3/2013 | Burnett | |
| 8,704,484 B2 | * | 4/2014 | Rosik et al. | 320/108 |
| 2010/0270970 A1 | * | 10/2010 | Toya et al. | 320/108 |
| 2011/0163714 A1 | * | 7/2011 | Ettes et al. | 320/108 |
| 2012/0032522 A1 | * | 2/2012 | Schatz et al. | 307/104 |
| 2012/0209085 A1 | | 8/2012 | Degen et al. | |
| 2012/0209165 A1 | | 8/2012 | Degen et al. | |
| 2013/0187619 A1 | * | 7/2013 | Dunipace | 323/225 |

FOREIGN PATENT DOCUMENTS

| | | |
|---|---|---|
| WO | WO-2009/091267 A2 | 7/2009 |
| WO | WO-2012/078230 A1 | 6/2012 |
| WO | WO-2012/112664 A1 | 8/2012 |

OTHER PUBLICATIONS

U.S. Appl. No. 13/397,498, filed Feb. 15, 2012, Degen et al.
PCT International Search Report and Written Opinion dated Aug. 19, 2014 in PCT Patent Application No. PCT/EP2014/055104.

* cited by examiner

*Primary Examiner* — Samuel Berhanu
(74) *Attorney, Agent, or Firm* — Foley & Lardner LLP; Christopher C. Bolten; Nicola A. Pisano

(57) ABSTRACT

Systems and methods are provided for regulating the transfer of energy inductively between an implantable device and an external charging system, wherein the energy transfer rate is regulated by varying an operating frequency of an inductive energy transfer circuit of the implantable device responsive a temperature measured within the implantable device.

15 Claims, 3 Drawing Sheets

SYSTEMS AND METHODS FOR REGULATING INDUCTIVE ENERGY TRANSFER TO AN IMPLANTABLE SYSTEM

FIELD OF THE INVENTION

The present invention is directed to the field of inductive charging of implantable devices, and more particularly, to regulating inductive charging of implantable devices to prevent excessive heat build-up or overcharging of a battery within the implantable device.

BACKGROUND OF THE INVENTION

There are many power-consuming devices designed to be implanted in the body of a human. Such devices frequently include a power source, such as a battery, that must be periodically recharged for the device to remain functional. Alternatively or additionally, an implantable device may receive operational power from an external charging system, for example, via an inductive charging circuit. For example, U.S. Patent Application Publication No. US 2012/0209165 A1 to Degen et al., assigned to the assignee of the present application, describes an example in which an implantable device, including an electro-mechanical pump is powered by a rechargeable battery, which is periodically recharged via an inductive charging circuit.

In the system described in the foregoing publication, energy is transmitted to a receiving circuit disposed within the implant by magnetically coupling a transmitting coil in an external charging system to a receiving coil in the implantable device. An alternating current flowing in the transmitting coil induces an alternating current to flow in the receiving coil. The current in the receiving coil is converted to a form suitable for recharging a battery disposed within the implantable device, or in some cases directly powering the electro-mechanical pump.

As described in the foregoing application, circuitry within the implantable device may heat up in response to the current flowing through the receiving coil or the voltage built up across the receiving coil, causing damage to the electromechanical components and circuitry disposed within the implantable device. Specifically, such heating may cause deterioration of the circuitry in the implantable device, or increased wear in mechanical components of the implantable device due to reduced clearances between components. Heating also may cause degradation of a humidity barrier over implant circuitry, thereby allowing moisture into the circuitry, possibly causing improper performance or implant damage. In addition, if the temperature of the circuitry increases too much, excessive heat may be transferred to the tissue surrounding the implantable device, causing discomfort or injury to that tissue.

In the system described in the foregoing application, the implantable device includes a temperature sensor disposed to monitor the battery temperature and a radio transceiver configured to transmit battery temperature data to the external charging system. A controller located within the external charging system is programmed to analyze the battery temperature reported by the implantable device, and to adjust the charging power supplied to inductive circuit of the external charging system to maintain the temperature of the implantable device below a predetermined threshold, e.g., less than 2° C. above body temperature. In one embodiment, the power supplied to the inductive coil of the external charging system is cycled between high power (e.g., 120 mA) and low power (e.g., 40 mA) charging intervals responsive to the measured temperature within the implantable device.

While the system described in the foregoing application effectively limits temperature transients experienced by the receiving circuit within the implantable device, it requires the use of the radio transceiver as a separate communications path to transmit temperature information to the external charging system, which information is in turn processed to intermittently reduce the power supplied to inductive circuit.

In view of the complexity of the inductive charging system described in the foregoing application, it would be desirable to provide an inductive charging system for an implantable device that directly regulates energy absorption of the receiving circuit of the implantable device, without the need for a separate communications path to an external charging system.

It further would be desirable to provide an inductive charging system for an implantable device that is capable of limiting temperature excursions within the receiving circuit of the implantable device by directly regulating energy absorption of the receiving circuit in real-time, without a time lag associated with transmission and analysis of data from the implantable device to an external charging system.

It still further would be desirable to provide circuits and methods for regulating energy absorption by the receiving circuit of an implantable device that reduce generation of ohmic heating within the receiving circuit.

SUMMARY OF THE INVENTION

In view of the drawbacks of previously-known inductive charging systems, the present invention provides an inductive charging system for an implantable device, and methods of us, that directly regulates energy absorption of the receiving circuit of the implantable device, without the need for a separate communications path to an external charging system.

In accordance with one aspect of the present invention, an inductive charging system for an implantable device, and methods of use, are provided that limit temperature excursions within the receiving circuit of the implantable device by directly regulating energy absorption of the receiving circuit in real-time, without a time lag associated with transmission and analysis of data from the implantable device to an external charging system.

In accordance with another aspect of the present invention, circuits and methods for regulating energy absorption by the receiving circuit of an implantable device are provided that reduce generation of ohmic heating within the receiving circuit.

An inductive charging circuit constructed in accordance with the principles of the present invention includes a receiving circuit disposed within an implantable device and a charging circuit disposed in an external charging system, such that energy is transferred between the charging circuit and receiving circuit predominantly when the circuits are tuned to a common resonant frequency. The implantable device may include a rechargeable power source, such as a battery, or capacitor, or may be configured to operate only when the receiving circuit is powered by the external charging system. The implantable device includes a sensor that monitors a portion of the implantable device, e.g., the temperature of the receiving circuit or rechargeable power source, and responsive to the sensor output, selectively adjusts an operating frequency of the receiving circuit so that it no longer absorbs energy transmitted by the charging circuit.

In some embodiments, the implantable device may include a microprocessor or dedicated logic for monitoring the sensor and adjusting parameters of the receiving circuit to reduce energy absorption by the receiving circuit.

Methods of adjusting inductive receiving circuits of implantable devices also are provided.

DETAILED DESCRIPTION OF THE PREFERRED EMBODIMENTS

Figure 1:
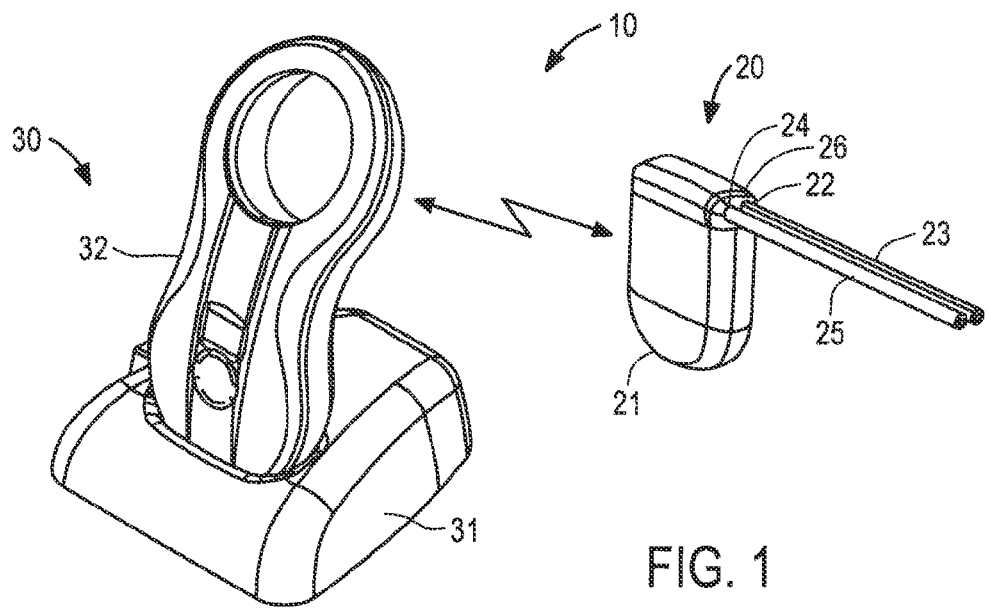
FIG. 1 depicts a previously-known system wherein an implantable device is selectively powered and/or recharged using an external charging system.
Figure 2A:
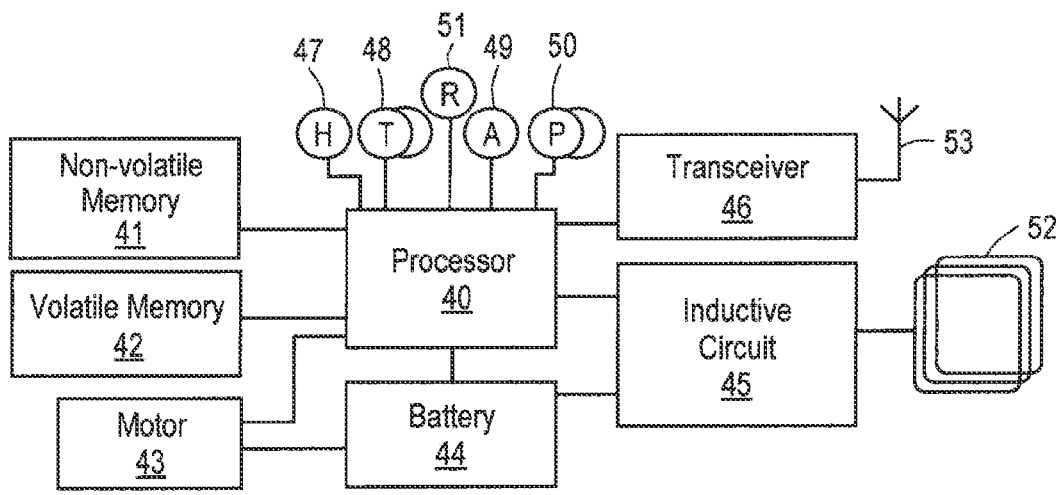
FIGS. 2A and 2B are, respectively, illustrative embodiments of an implantable device and external charging system suitable for use with the present invention.
Figure 2B:
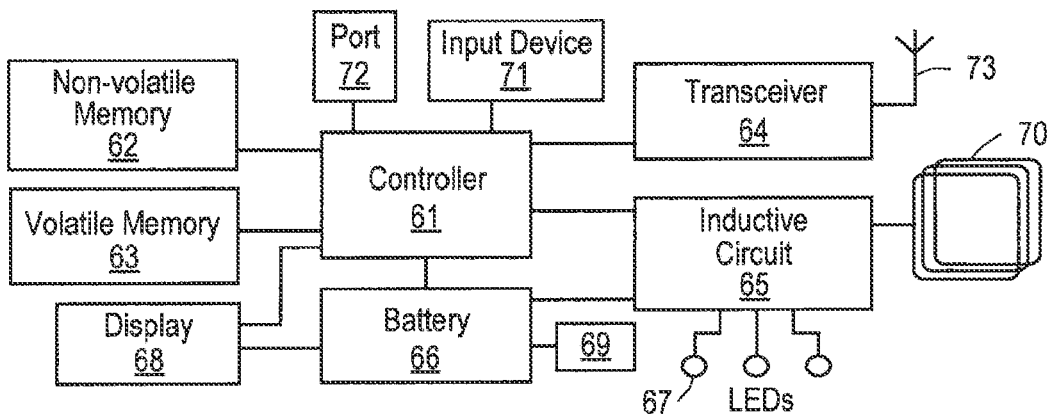

Referring to FIGS. 1, 2A and 2B, an exemplary embodiment of a system suitable for use with the inductive charging system of the present invention is described. System 10 is similar to that described in U.S. Patent Application Publication No. US 2012/0209165 A1 to Degen et al., assigned to the assignee of the present application, the entirety of which is incorporated herein by reference. System 10 illustratively comprises implantable device 20, and external charging system 30. As described in the incorporated application, system 10 also may include a monitoring and control system (not shown) that communicates with external charging system. As will be understood, implantable device 20 is configured to be implanted subcutaneously within a human body, while external charging system 30 is configured to be periodically placed over the skin in the vicinity of the implantable device to charge and communication with the implantable device.

Implantable device 20 illustratively comprises an electromechanical pump having housing 21 configured for subcutaneous implantation. In one embodiment suitable for treating ascites, implantable device 20 includes an electrically-driven mechanical gearpump having inlet port 22 coupled to peritoneal catheter 23 and outlet port 24 coupled to bladder catheter 25. Peritoneal catheter 23 comprises a tube having a first end configured to be coupled to pump inlet 23 and a second end configured to be positioned in a patient's peritoneal cavity. Bladder catheter 25 comprises a tube having a first end configured to be coupled to pump outlet 24 and a second end configured to be inserted through the wall of, and fixed within, a patient's bladder. Peritoneal catheter 23 and bladder catheter 25 are coupled to pump housing 21 using connector 26 configured to reduce the risk of improper installation and inadvertent disconnection, and may in addition include distinct cross-sections that reduce the risk of improper installation.

External charging system 30 illustratively comprises base 31 and handpiece 32. Handpiece 32 may house a controller, a radio transceiver, an inductive charging circuit, a battery, a quality-of-charging indicator and a display, and is removably coupled to base 31 to recharge its battery. Base 31 may contain a transformer and circuitry for converting conventional 120V power service to a suitable DC current to charge handpiece 32 when coupled to base 31. Alternatively, handpiece 32 may include such circuitry and a detachable power cord that permits the handpiece to be directly plugged into a convention 120V wall socket to charge the battery.

Referring now to FIGS. 2A and 2B, schematic diagrams of exemplary functional blocks implantable device 20 and external charging system 30 are described. As set forth in greater detail below, implantable device 20 may be adapted from that described in the above-incorporated application to implement the present invention.

In particular, in FIG. 2A, implantable device 20 includes control circuitry, illustratively processor 40 coupled to nonvolatile memory 41, such as flash memory or electrically erasable programmable read only memory, and volatile memory 42 via data buses. Processor 40 is electrically coupled to electric motor 43, battery 44, inductive circuit 45, radio transceiver 46 and a plurality of sensors, including humidity sensor 47, a plurality of temperature sensors 48, accelerometer 49, a plurality of pressure sensors 50, and respiratory rate sensor 51. Inductive circuit 45 is electrically coupled to coil 52 to receive energy transmitted from external charging system 30, while transceiver 46 is coupled to antenna 53, and likewise is configured to communicate with a transceiver in external charging system 30, for example, to transmit information relating functioning of the implantable device to the external charging system. All of the components depicted in FIG. 2A are contained within a low volume sealed biocompatible housing, as shown in FIG. 1.

Processor 40 executes firmware stored in nonvolatile memory 41 which controls operation of motor 43 responsive to signals generated by motor 43, sensors 47-51 and commands received from transceiver 46. Processor 40 also controls reception and transmission of messages via transceiver 46 and operation of inductive circuit 45 to charge battery 44. Inductive circuit 45 is configured to recharge battery 44 of the implantable device when exposed to a magnetic field supplied to coil 52 by a corresponding inductive circuit within handpiece 32 of external charging system 30. In addition, inductive circuit 45 optionally may be configured not only to recharge battery 44, but to directly provide energy to motor 43 in a "boost" mode or jog/shake mode to unblock the pump. Additional operational details relating to the components of implantable device 20 are available in the above-incorporated application.

Referring to FIG. 2B, handpiece 32 of external charging system 30 contains controller 61, illustratively the processor of a micro-controller unit coupled to nonvolatile memory 62 (e.g., either EEPROM or flash memory), volatile memory 63, radio transceiver 64, inductive circuit 65, battery 66, indicator 67 and display 68. Controller 61, memories 62 and 63, and radio transceiver 64 may be incorporated into a single microcontroller unit, such as the MPS430 family of microprocessors, available from TEXAS INSTRUMENTS INCORPORATED™, Dallas, Tex., Transceiver 64 is coupled to antenna 73 for sending and receiving information to implantable device 20. Battery 66 is coupled to connector 69 that removably couples with a connector in base 31 to recharge the battery. Inductive circuit 65 is coupled to coil 70. Input device 71, preferably a multi-function button, also is coupled to controller 61 to enable a patient to input a number of commands. Indicator 67 illustratively comprises a plurality of LEDs that illuminate to indicate the quality of charge coupling achieved between the handpiece and implantable device, and therefore assist in optimizing the positioning of handpiece 32 relative to the implantable device during recharging.

Controller 61 executes firmware stored in nonvolatile memory 62 that controls communications and charging of the implantable device. Controller 61 preferably is configured to transfer and store data, such as event logs, uploaded to handpiece 32 from the implantable device, for download and review via port 72 during physician office visits. Controller 61 also may include firmware for transmitting commands input using input device 71 to the implantable device, and monitoring operation of the implantable device during execution of such commands, for example, during boost or jogging/shaking operation of the gearpump to clear a blockage. In addition, controller 61 controls and monitors various power operations of handpiece 32, including operation of inductive circuit 65 during recharging of the implantable device, displaying the state of charge of battery 66, and controlling charging and display of state of charge information for battery 44.

Inductive circuit 65 is coupled to coil 70, and is configured to inductively couple with coil 52 of the implantable device to recharge battery 44 of the implantable device. Energy transfer is accomplished via electromagnetic coupling of coil 70 with coil 52 in the implantable device. As will be appreciated by one of ordinary skill, an alternating current is delivered through coil 70, which causes an electromagnetic field to be established around coil 70, which induces an alternating current in coil 52. The design of coils 52 and 70 and corresponding inductive circuits 45 and 65 determines the necessary orientation and distance between the coils for effective energy transfer. In a preferred embodiment, inductive coils 52 and 70 are capable of establishing good coupling through a gap of 35 mm, when operating at a frequency of 315 kHz or less. Inductive circuit 65 optionally is coupled to indicator 67 that lights to indicate the extent of magnetic coupling between coils 52 and 70 (and thus quality of charging), thereby assisting in positioning handpiece 32 relative to the implantable device.

As described in the above-incorporated application, the temperature of battery 44, inductive circuit 45 and/or implantable device 20 may be measured by sensor 48 and transmitted under the control of processor 40 to external charging system 30, which adjusts the power supplied to inductive circuit 65 to prevent transmission of excessive energy to implantable device 20. While this system has been demonstrated to be effective in retaining battery and implant temperatures within 2° C. band during operation, it requires use of both radio transceivers 46 and 65 and involves some time-lag. In accordance with the principles of the present invention, these limitations are overcome by including an element under the control of processor 40, or embedded directly within inductive circuit 45 that selectively reduces energy absorption by inductive circuit 45 of the implantable device to maintain a desired temperature range within implantable device 20.

In accordance with the principles of the present invention, the energy transfer rate between inductive circuits 45 and 65 may be decreased by detuning the resonance frequency of inductive circuit 45. Detuning of inductive circuit 45 of implantable device 20 may be achieved, for example, by modifying the impedance of the inductive circuit to move its resonant frequency away from the resonant frequency of inductive circuit 65. In some implementations, the temperature of battery 44 and/or inductive circuit 45 may be monitored by temperature sensor 48 and processor 40, such that when the measured temperature exceeds a threshold value (e.g., 2° above body temperature), the processor generates and output that modifies the resonance parameters of inductive circuit 45. Alternatively, electronic components employed within inductive circuit may have temperature dependent properties that automatically adjust the resonance parameters of inductive circuit 45 to limit the rate of energy transfer responsive to the temperature experienced by such components.

Figure 3:
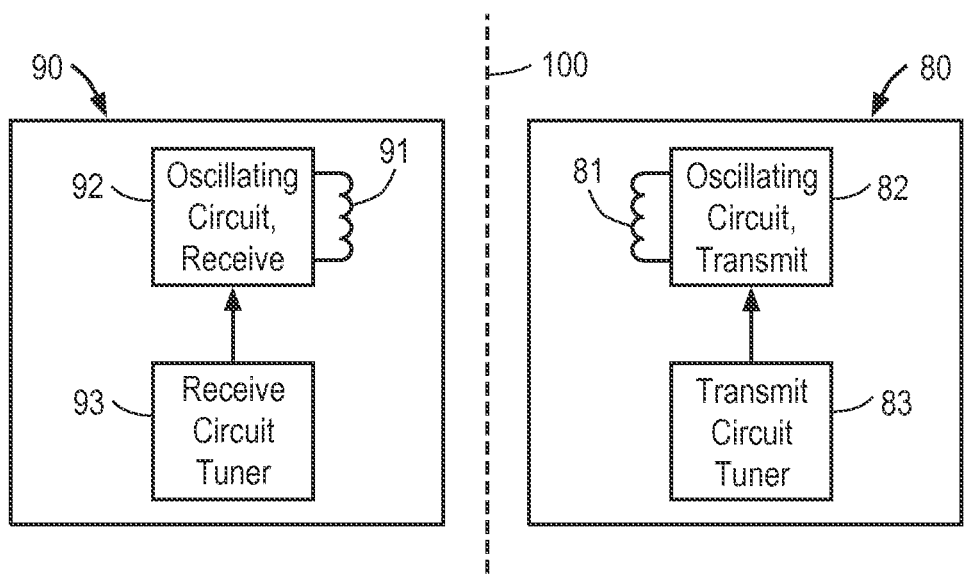
FIG. 3 is an generalized schematic illustrating recharging of an internal energy storage using an external charging system.

Referring now to FIG. 3, a generalized system for transferring energy from external charging system 80 to implantable device 90 across barrier 100 (e.g., skin) is described. External charging system 80 includes transmit coil 81, transmit oscillating circuit 82, and optionally, transmit circuit tuner 83. Implantable device 90 includes receive coil 91, receive oscillating circuit 92, and receive circuit tuner 93. As discussed above, coils 81 and 91, when coupled, may be mathematically modeled as a transformer, meaning that in addition to the individual conductances of the coils, there is also a mutual inductance created by the coupling of the coils.

In the ideal case, implantable device 90 is configured for maximum energy transfer when the inductance of receive coil 91, the mutual inductance seen from receive coil 91, and the impedance of receive oscillating circuit 92 together form a resonant circuit. In the ideal case, external charging circuit 80 is configured for maximum energy transfer when the inductance of transmit coil 81, the mutual inductance seen from transmit coil 81, and the impedance of transmit oscillating circuit 82 together form a resonant circuit. "Maximum energy transfer" as used herein is the maximum energy available at the time of energy transfer between devices 80 and 90 when operating in the intended environment. However, as will be appreciated, most systems actually operate in a non-ideal manner, as there are many factors that influence rate of energy transfer other than those described.

There is a rather substantial typically narrow bandwidth peak of energy at the resonance frequency in the frequency response of a circuit, and less energy at neighboring frequencies. A small change in frequency near the resonant frequency results in a large change in energy. This feature allows for coarse energy transfer rate control. Away from the resonance frequency, the difference in energy between two nearby frequencies in the frequency response of a circuit may be comparatively small, such that a small change in frequency results in a small change in energy. This feature allows for fine energy transfer rate control.

In the ideal case, energy transfer may be maximized when both device 90 and external charging system 90 operate at resonance and the resonant frequency of device 90 is equal to the resonant frequency of external charging system 80. Energy transfer may be reduced from maximum by detuning one or both of device 90 and system 80 away from a common resonant frequency. For example, the resonant frequency of device 90 or system 80 may be changed such that their resonant frequencies are no longer substantially equal. Energy transfer also may be reduced from maximum by operating system 80 at a frequency other than its resonant frequency, thereby decreasing the energy available for transfer.

Receive oscillating circuit 92 may include at least one variable electrical component whose value may be changed to change the resonance of device 90. Transmit oscillating circuit 82 also may include at least one variable electrical component whose value may be changed to change the resonance or the operating frequency of system 80.

Figure 4A:
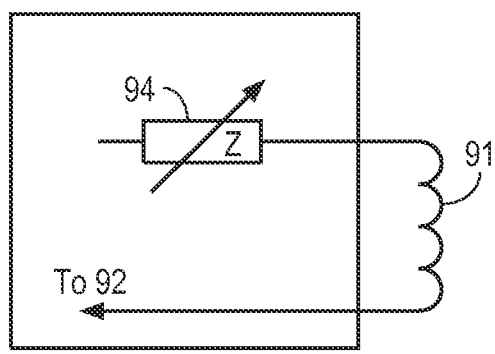
FIGS. 4A and 4B are, respectively, exemplary embodiments of receiver inductive circuit with variable series impedance.
Figure 4B:
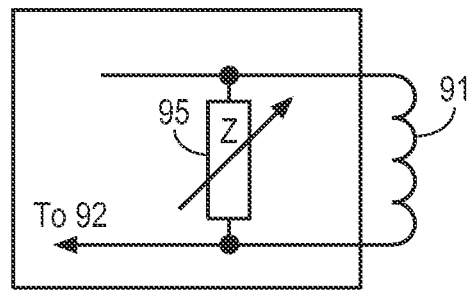

FIG. 4A illustrates an example where receive oscillating circuit 91 of implantable device 90 includes variable impedance 94 in series with receive coil 91, where impedance 94 may be a combination of resistance, inductance, and capacitance. There are several ways to vary impedance, including but not limited to selecting portions of a structure such as a resistive ladder, or switching in additional components. FIG. 4B illustrates an alternative embodiment of receive oscillating circuit 91, in which variable impedance 95 is disposed in parallel with receive coil 91, where impedance 95 may be a combination of resistance, inductance, and capacitance. One example of variable impedance 95 is a low-resistance element, or a short circuit, which is selected to substantially or completely stop energy transfer. As a further alternative, receive oscillating circuit 91 may include both series and parallel variable impedances. In this case, by varying the impedance of a series or parallel impedance or both, the operating and/or resonant frequency of the receive side will shift away from the resonant frequency of the transmit side, thereby reducing the rate of energy transfer between external charging circuit 80 and implantable device 90.

Figure 5:
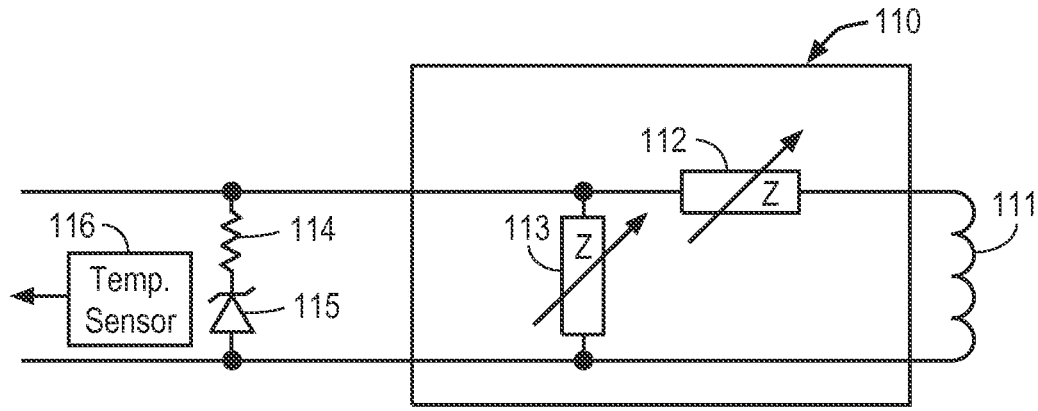
FIG. 5 depicts and exemplary circuit for detecting and limiting energy transfer during over-temperature conditions.

Referring now to FIG. 5, an exemplary circuit for regulating energy transfer to an implantable device responsive to temperature sensed within the device is described. Oscillating circuit 110 having coil 111 is shown as including a combination of variable impedances 112 and 113 although none of the impedances of circuit 110 need be variable. Resistive component 114 and zener diode 115 in series are placed across the output of oscillating circuit 110 to limit the voltage at that point for protection of circuitry in receiver the implantable device. Temperature sensor 116 is placed adjacent to zener diode 115 to measure the temperature of the area around zener diode 115. In some implementations, temperature sensor 116 may be fabricated in an integrated circuit including the zener diode 115. As the voltage increases at the output of oscillating circuit 110, current through zener diode 115 increases, and the temperature of zener diode 115 increases correspondingly. In accordance with one aspect of the present invention, the temperature of zener diode 115 may be input to a comparator or processor where it is compared to a threshold value, and if the temperature is observed to exceed the threshold, one or both of the impedances 112 and 113 may be adjusted to change the resonant frequency of oscillating circuit 110, thus reducing absorption of energy transmitted by the external charging system. In this manner, the temperature of zener diode 115 may be used as feedback in the energy transfer control loop to limit the rate of energy transfer through coil 111 and thereby keeps the temperature of oscillating circuit 110 and the implantable device at an acceptable level.

Figure 6:
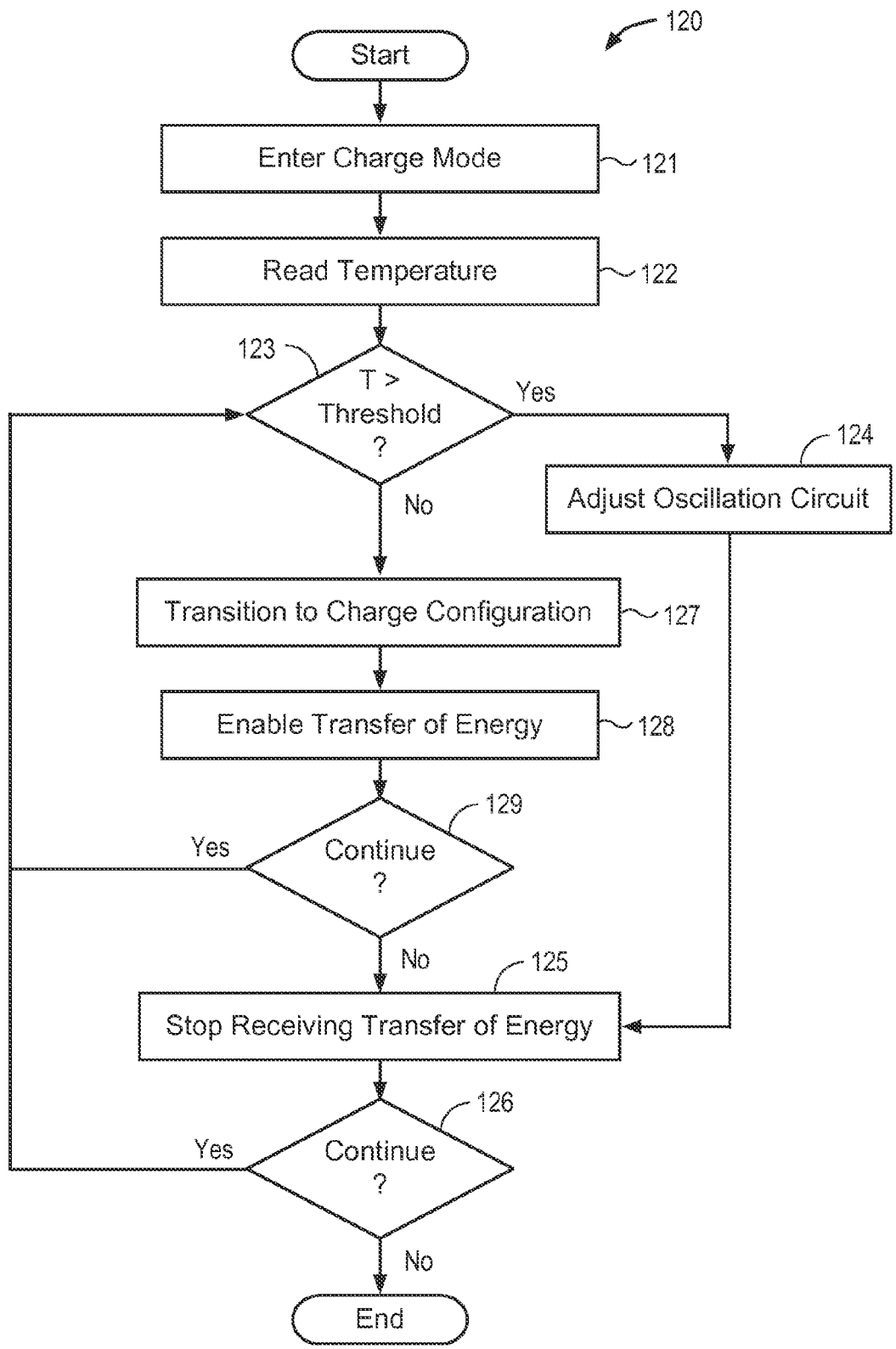
FIG. 6 illustrates an example method for limiting energy transfer within an implantable device.

Referring FIG. 6, an illustrative method 120 for regulating energy transfer in an inductive charging circuit, such as depicted in FIGS. 3 and 5 above, using temperature feedback is described.

Method 120 begins at block 121 when the implantable device 90 enters charge mode, which may occur when external charging system 80 is proximate to implantable device 90.

At block 122, temperature sensor 116 is read. Temperature may be read, for example, by a processor, such as processor 40 depicted in FIG. 2A, or temperature may be interfaced through an analog or digital circuit such that the processor receives inputs or interrupts indicating a temperature, a temperature range, or that temperature has crossed a threshold.

At decision block 123, if the measured temperature has crossed a predefined threshold, method 120 continues at block 124 where receive circuit tuner 93 adjusts oscillating circuit 92 to limit or stop energy transfer, at block 125. If, at decision block 126, after a predetermined interval the battery in implantable device 90 still is not fully charged, then temperature is cannot checked at decision block 123. If on the other hand the battery is fully charged, method 120 ends.

If the measured temperature at block 123 is below the predefined threshold, method 120 continues at block 127, where oscillating circuit 92 transitions to charge configuration, e.g., by adjusting either or both impedances 112 and 113 so that the resonant frequency of oscillating circuit 110 and coil 111 again match the resonant frequency of external charging system 80, thereby enabling energy transfer at block 128.

At decision block 129, if processor determines that energy transfer is to continue, method 120 repeats, beginning at decision block 123. Otherwise, method 120 continues at block 125 to discontinue the transfer of energy. At block 126 the charging state of the battery within the implantable device is again checked, and if the charge is complete, method 120 ends.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An implantable device configured to be inductively charged or powered by an external charging system having a resonant frequency, the implantable device comprising:
   an inductive energy transfer circuit having an oscillating circuit and an operating frequency;
   a battery coupled to the inductive energy transfer circuit;
   an electrical component coupled to the oscillating circuit and configured to create a short circuit when a temperature of the electrical component exceeds a threshold value, the short circuit causing the operating frequency to shift away from the resonant frequency, thereby regulating an amount of energy delivered to the battery by the inductive energy transfer circuit.

2. The implantable device of claim 1, wherein the implantable device further comprises a pump configured to be powered by the battery.

3. The implantable device of claim 1, wherein the electrical component comprises an adjustable impedance, and an increase in a temperature of the adjustable impedance is configured to adjust the adjustable impedance to shift the operating frequency.

4. The implantable device of claim 3, wherein the inductive energy transfer circuit includes a coil, and the adjustable impedance is connected in series with the coil.

5. The implantable device of claim 3, wherein the inductive energy transfer circuit includes a coil, and the adjustable impedance is connected in parallel with the coil.

6. The implantable device of claim 2, wherein the implantable device further comprises an inlet catheter comprising an inlet end configured to be implanted in a peritoneal cavity and an outlet catheter comprising an outlet end configured to be implanted in a bladder, and
   wherein the pump is configured to pump fluid from the peritoneal cavity via the inlet catheter to the bladder via the outlet catheter.

7. The implantable device of claim 1, wherein the implantable device further comprises a transceiver configured to communicate with the external charging system.

8. A kit comprising the implantable device of claim 1 and the external charging system.

9. The kit of claim 8, wherein the external charging system comprises a base and a handpiece.

10. A method of regulating energy transfer in an implantable device configured to be inductively charged or powered by an external charging system having a resonant frequency, the method comprising:

providing the implantable device comprising an inductive energy transfer circuit having an oscillating circuit, an operating frequency, a battery, and an electrical component coupled to the oscillating circuit, the electrical component configured to create a short circuit when a temperature of the electrical component exceeds a threshold value;

creating a short circuit that shifts the operating frequency away from the resonant frequency when the temperature of the electrical component exceeds the threshold value, thereby regulating an amount of energy delivered to the battery by the inductive energy transfer circuit.

11. The method of claim 10, wherein the implantable device further comprises a pump.

12. The method of claim 10, wherein the electrical component comprises an adjustable impedance.

13. The method of claim 11, wherein the implantable device comprises an inlet port coupled to an inlet catheter, and an outlet port coupled to an outlet catheter, the method further comprising pumping a fluid from the inlet catheter to the outlet catheter.

14. The method of claim 10, wherein the implantable device further comprises a transceiver configured to communicate with the external charging system.

15. The method of claim 10, wherein the external charging system comprises a base and a handpiece.

* * * * *